United States Patent [19]

Langford

[11] Patent Number: 4,978,806

[45] Date of Patent: Dec. 18, 1990

[54] SCALE-UP AND SYNTHESIS OF 1-METHOXYCYGLOHEPTA-1,3,5-TRIENE

[75] Inventor: Gordon E. Langford, Edmonton, Canada

[73] Assignee: Her Majesty the Queen in right of Canada, as represented by the Minister of National Defence of Her Majesty's Canadian Government, Canada

[21] Appl. No.: 441,511

[22] Filed: Nov. 27, 1989

[30] Foreign Application Priority Data

Jan. 24, 1989 [CA] Canada ................................. 589473

[51] Int. Cl.$^5$ ...................... C07C 41/00; C07C 43/18
[52] U.S. Cl. ..................................... 568/667; 568/669
[58] Field of Search ................................ 568/667, 669

[56] References Cited

U.S. PATENT DOCUMENTS 4,249,025  6/1981  Hydro .................................. 568/669
4,506,102  3/1985  Kaufhold et al. .................... 568/667

OTHER PUBLICATIONS

Gogery et al., "Canadian Jour. Chem.", 29:938–945 (1951).
Garbisch, "J. Org. Chem.", vol. 30, p. 2109 (1965).
Parham et al., "J. Amer. Chem. Soc.", vol. 84, p. 1755 (1962).
Lindsey et al., "Tetrahedron", vol. 21, p. 1673 (1965).

*Primary Examiner*—Werren B. Lone
*Attorney, Agent, or Firm*—Nixon & Vanderhye

[57] ABSTRACT

A method for preparation of 1-methoxycyclohepta-1,3,5-triene in commercial quantities, which comprises the steps of heating 7,7-dichloro-1-methoxybicyclo[4.1.0]heptane in a refluxing reaction solvent comprising a lower boiling aromatic amine, at reflux, until suitable amounts of 1-methoxycyclohepta-1,3,5-triene have been produced, and recovering the 1-methoxycyclohepta-1,3,5-triene. Suitable reaction solvents include 2-picoline, pyridine and 2,6-lutidine. The method according to the present invention results in safer temperature control in the production of 1-methoxycyclohepta-1,3,5-triene, and increased yields.

8 Claims, No Drawings

SCALE-UP AND SYNTHESIS OF 1-METHOXYCYGLOHEPTA-1,3,5-TRIENE

BACKGROUND OF THE INVENTION

The present invention relates to an improved method of producing 1-methoxycyclohepta-1,3,5-triene.

1-methoxycyclohepta-1,3,5-triene is a relatively non-toxic compound, gaseous at room temperature, which is used for the training of troops for defence purposes. As this gas has mild effects similar to those of "tear gas" on humans, troops may be trained, for example, in the proper use of gas masks in environments in which 1-methoxycyclohepta-1,3,5-triene has been introduced.

1-ethoxy-1,3,5-cycloheptatriene has been previously prepared in 37% yield by heating 7,7-dichloro-1-ethoxybicyclo[4.1.0]heptane in quinoline for about 10 minutes at 160° C. –180° C. (W. E. Parham et al., *J.A.C.S.*, 84, 1755 (1962) and W. E. Parham et al., *J.A.C.S.*, 87, 321 (1965)). The reaction is exothermic. Extending the heating time to 45 minutes resulted in a yield of only 5%. Similarly 1-methoxycyclohepta-1,3,5-triene has been made in 33% yield by heating 7,7-dibromo-1-methoxybicyclo[4.1.0]heptane in quinoline for 1 hour at 150° C. (D. G. Lindsey and C. B. Reese, *Tetrahedron*, 21, 1673 (1965)).

Use of other aromatic bases instead of quinoline has been reported in the literature, but none of the desired product was reported. Refluxing 7,7-dichloro-1-ethoxybicyclo[4.1.0]heptane in pyridine for 75 minutes has produced 2-ethoxy-3-chloro-1,3-cycloheptadiene in 85% yield (W. E. Parham et al., *J.A.C.S.*, 84, 1755 (1962) and W. E. Parham et al., *J.A.C.S.*, 87, 321 (1965)). When 7,7-dibromo-1-methoxybicyclo[4.1.0]heptane is heated in 2,6-lutidine for 45 minutes at 135° C., methoxybromocycloheptadienes were obtained in 70% yield (D. G. Lindsey and C. B. Reese, *Tetrahedron*, 21, 1673 (1965)).

Alternative methods of production of 1-methoxycyclohepta-1,3,5-triene have been reported. It has been made from cycloheptanone ketals by bromination and elimination (E. W. Garbisch, Jr., *J. Org. Chem.*, 30, 2109 (1965)). 1-methoxycyclohepta-1,3,5-triene has also been made from tropylium tetrafluoroborate (W. R. Hydro, U.S. Pat. No. 4,249,025 (1981), G. A. Grant, Canadian Pat. No. 1,172,957 (1984)). It has been reported that the yield of this process is improved by adding a stabilizer, phenothiazine, to the reaction mixture (W.R. Hydro, U.S. Pat. No. 4,249,025 (1981)).

There are four possible isomers of 1-methoxyclohepta-1,3,5-triene, but it has been shown that the isomers interconvert thermally (E. Weth and A. S. Dreiding, *Proc. Chem. Soc.*, 59 (1964), and T. Nozoe and K. Takahashi, *Bull. Chem. Soc. Jap.*, 38, 665 (1965)). The equilibrium mixture at 150° C. consists of the 1-methoxy-,2-methoxy-, and 3-methoxy- isomers in the ratio 100:1:10 (E. Weth and A. S. Dreiding, *Proc. Chem. Soc.*, 59 (1964)). None of the 7-methoxyisomer is found at equilibrium.

In experiments leading up to the present invention, it was attempted to produce 1-methoxycyclohepta-1,3,5-triene from 7,7-dichloro-1-methoxybicyclo[4.1.0]heptane. However, even after optimizing the reaction time and temperature, the reaction in quinoline gave only about 50% yield of 1-methoxycyclohepta-1,3,5-triene, with extensive tarry by-products. More seriously, the reaction could not be scaled-up safely. It was found that in large batches, exothermic reaction accompanied by exothermic decomposition of the product could cause the temperature to rise uncontrollably. For safe operation, the temperature should be kept below 150° C., but the high boiling point of quinoline (238° C.) allows the temperature to rise much higher.

SUMMARY OF THE INVENTION

In accordance with the present invention, 1-methoxycyclohepta-1,3,5-triene is prepared according to a method which comprises the steps of heating 7,7-dichloro-1-methoxybicyclo[4.1.0]heptane in a refluxing reaction solvent comprising a lower boiling aromatic amine, at reflux, until suitable amounts of 1-methoxycyclohepta-1,3,5-triene have been produced, and recovering the 1-methoxycyclohepta-1,3,5-triene. It is preferred that the reaction solvent be selected from the group consisting of 2-picoline, pyridine and 2,6-lutidine, the solvent being chosen to have a boiling point of about 130° C. 2-picoline is the preferred reaction solvent. It is also preferred to include, in the reaction mixture, phenothiazine as a stabilizer to minimize polymerization during the reaction. For best results, it is preferred that the moisture of the reaction mixture be less than 0.2%.

DESCRIPTION OF PROCESS ACCORDING TO THE PRESENT INVENTION

By choosing a solvent with a boiling point of about 130° C., the reaction takes place in the safe operating range. The reaction is run at reflux. Under these conditions thermal run-away is not possible. The reaction, in refluxing 2-picoline, is complete in about 20 hours. To minimize decomposition of the product during this prolonged heating, phenothiazine is added as a stabilizer. Since traces of water in the reaction mixture also appear to cause a serious loss of yield, for best results the moisture content of the reaction mixture should be held to less than 0.2% by weight.

Pyridine and 2,6-lutidine have also been successfully used as reaction solvents. 2-picoline however seems to give the best yield, gc yields over 85% and isolated yields over 70% having been obtained using 2-picoline.

The improved process of the present invention has advantages over prior art processes in that:

(1) Use of a refluxing solvent ensures safe temperature control.

(2) The process of the present invention provides a prolonged reaction time under mild conditions. Such conditions are less difficult and less dangerous to scale-up over prior art methods which used reaction times of, for example 10 minutes to 1 hour at relatively high temperatures. The prolonged reaction time of the present invention also ensures equilibrium of the possible 1-methoxycyclohepta-1,3,5-triene isomers (E. Weth and A. S. Dreiding, *Proc. Chem. Soc.*, 59 (1964) and T. Nozoe and K. Takahashi, *Bull. Chem. Soc. Jap.*, 38, 665 (1965)). This equilibrium leads to the production of material of consistent quality.

(3) Use of a stabilizer minimizes polymerization during the reaction.

(4) Use of reaction mixtures containing less than 0.2% water minimizes the deleterious effect of moisture on the yield of this reaction.

EXAMPLE

A solution of 7,7,-dichloro-1-methoxybicyclo[4.1.0-]heptane (500 g) and phenothiazine (2 g) in 2-picoline (1500 g), was heated under reflux (128°–130° C.) for 20 hours under a nitrogen atmosphere. After cooling to room temperature, quinoline (662 g) and phenothiazine (2 g) were added, and then the mixture was distilled at 20 mm Hg until the head temperature rose to 102° C. The distillate was treated with phenothiazine (2 g) and then fractionally redistilled at 20 mm Hg. 1-Methoxy-cycloheptatriene was collected at 70°–73° C. The yield was 193.9 g (62%).

Thus, it is apparent that there has been provided in accordance with present invention a method for preparation of 1-methoxycyclohepta-1,3,5-triene that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

The embodiments of the invention in which an exclusive property or privilege is claimed are defined as follows:

1. A method for preparation of 1-methoxycyclohepta-1,3,5-triene which comprises the steps of heating 7,7-dichloro-1-methoxybicyclo[4.1.0]heptane in a refluxing reaction solvent comprising a lower boiling aromatic amine, at reflux, until suitable amounts of 1-methoxycyclohepta-1,3,5-triene have been produced, and recovering the 1-methoxycyclohepta-1,3,5-triene.

2. A method according to claim 1 wherein the reaction solvent is selected from the group consisting of 2-picoline, pyridine and 2,6-lutidine.

3. A method according to claim 1 wherein the reaction solvent is 2-picoline.

4. A method according to claim 1, wherein the reaction mixture includes phenothiazine as a stabilizer to minimize polymerization during the reaction.

5. A method according to claim 1, wherein the reaction mixture includes phenothiazine as a stabilizer to minimize polymerization during the reaction, and wherein the moisture content of the reaction mixture is less then 0.2% water.

6. A method according to claim 1 wherein the reaction solvent is pyridine.

7. A method according to claim 1 wherein the reaction solvent is 2,6-lutidine.

8. A method according to claim 1 wherein the reaction takes place for about 20 hours at a temperature of about 130° C.

* * * * *